(12) United States Patent
Deaver et al.

(10) Patent No.: US 9,517,235 B2
(45) Date of Patent: *Dec. 13, 2016

(54) METHODS FOR TREATING ANTIPSYCHOTIC-INDUCED WEIGHT GAIN

(71) Applicant: Alkermes Pharma Ireland Limited, Dublin (IE)

(72) Inventors: Daniel Deaver, Franklin, MA (US); Mark Todtenkopf, Franklin, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/813,260

(22) Filed: Jul. 30, 2015

(65) Prior Publication Data
US 2016/0051538 A1     Feb. 25, 2016

Related U.S. Application Data

(63) Continuation of application No. 14/297,171, filed on Jun. 5, 2014, now Pat. No. 9,126,977, which is a continuation of application No. 13/215,718, filed on Aug. 23, 2011, now Pat. No. 8,778,960.

(60) Provisional application No. 61/376,120, filed on Aug. 23, 2010.

(51) Int. Cl.
| | |
|---|---|
| *A61K 31/554* | (2006.01) |
| *C07D 221/28* | (2006.01) |
| *C07D 405/06* | (2006.01) |
| *A61K 31/485* | (2006.01) |
| *A61K 31/439* | (2006.01) |
| *A61K 31/496* | (2006.01) |
| *A61K 31/519* | (2006.01) |
| *A61K 31/5513* | (2006.01) |

(52) U.S. Cl.
CPC .......... *A61K 31/485* (2013.01); *A61K 31/439* (2013.01); *A61K 31/496* (2013.01); *A61K 31/519* (2013.01); *A61K 31/554* (2013.01); *A61K 31/5513* (2013.01); *C07D 221/28* (2013.01); *C07D 405/06* (2013.01)

(58) Field of Classification Search
IPC ................ A61K 31/485,31/439, 31/496; C07D 221/28, 405/06
See application file for complete search history.

*Primary Examiner* — Shirley V Gembeh
(74) *Attorney, Agent, or Firm* — Elmore Patent Law Group, P.C.; Carolyn S. Elmore; Joseph C. Zucchero

(57) ABSTRACT

The present invention relates to the discovery of a novel opioid modulator effective in reducing pharmacologically induced weight gain associated with atypical antipsychotic use. The present invention provides methods of reducing antipsychotic induced weight gain, methods for suppressing food intake and reducing ghrelin levels induced by atypical antipsychotic medications in a patient.

12 Claims, 6 Drawing Sheets

(a) Olanzapine (b) Olanzapine + Compound 1

METHODS FOR TREATING ANTIPSYCHOTIC-INDUCED WEIGHT GAIN

RELATED APPLICATIONS

This application is a continuation of U.S. application Ser. No. 14/297,171, filed Jun. 5, 2014, which is a continuation of U.S. application Ser. No. 13/215,718, filed Aug. 23, 2011, now U.S. Pat. No. 8,778,960, issued Jul. 15, 2014, which claims the benefit of U.S. Provisional Application No. 61/376,120, filed on Aug. 23, 2010. The entire teachings of the above applications are incorporated herein by reference.

FIELD OF INVENTION

The present invention relates to medications used for weight control. More particularly, the present invention relates to the use of a novel opioid receptor modulator to minimize weight gain associated with antipsychotic drugs.

BACKGROUND OF INVENTION

Antipsychotic medications are among the most important therapeutic tools for treating various psychotic disorders. There are two categories of antipsychotics, typical and atypical. Typical antipsychotics e.g., haloperidol and chlorpromazine, were first developed in the 1950's and were used to treat psychosis, particularly schizophrenia. Common side effects of typical antipsychotics include: dry mouth, tremors, weight gain, muscle tremors, and stiffness. In addition, typical antipsychotics yield extrapyramidal side effects. These side effects include: motor disturbances, parkinsonian effects, akathesia, dystonia, akinesia, tardive dyskinesia, and neuroleptic malignant syndrome. Some of these side effects have been described to be worse than the actual symptoms of schizophrenia. Atypical antipsychotics are considered to be the first line of treatment for schizophrenia because of the improved extrapyramidal side effect profile in comparison to typical antipsychotics. Atypical antipsychotics are also associated with superior tolerability, adherence and relapse prevention and have led to improved treatment for patients with serious mental illness. However, they are also associated with significant weight gain. Numerous reports based on extensive clinical studies have reported that 40-80% of patients under chronic atypical antipsychotic treatment experience substantial weight gain, ultimately exceeding their ideal body weight by 20% (Umbricht et al., *J Clin. Psychiatry* 55 (Suppl. B):157-160; Baptista, *Acta Psychiatr. Scand.* 100:3-16, 1999). Weight gain was found to be greatest with clozapine, olanzapine, risperidone, and quetiapine, and less with aripiprazole and ziprasidone. (Taylor et al., *Acta Psychiatr Scand.* 2001 February; 103(2):158). Weight gain associated with atypical antipsychotics increases the risk of obesity in patients undergoing treatment. Obesity is a leading cause of mortality as it frequently leads to conditions such as diabetes and cardiovascular disorders. In addition, atypical antipsychotics are increasingly prescribed to children and adolescents with psychiatric disorders. A recent study reported that young children who take antipsychotics risk long term health risks associated with rapid weight gain, for example, metabolic changes that could lead to diabetes, hypertension and other illnesses. (Varley et al., *JAMA.* 2009; 302(16):1811-1812).

Excessive weight gain associated with atypical antipsychotic use is a significant issue given its impact on general health and psychological issues. Unwanted weight gain is also one of the most common reasons for a patient's non-compliance of an atypical antipsychotic administration schedule, ultimately leading to the failure of the treatment. Therefore, there is a continuing need to identify and develop more effective drug treatments for preventing or reducing this side effect of atypical treatment.

SUMMARY OF INVENTION

Applicants have surprisingly discovered that compounds of Formula I are effective in reducing pharmacologically induced weight gain associated with atypical antipsychotic use.

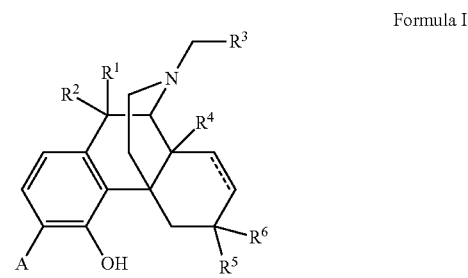

Formula I wherein,
A is chosen from —C(=O)NH$_2$ and —C(=S)NH$_2$;
$R^1$ and $R^2$ are both hydrogen or taken together $R^1$ and $R^2$ are =O;
$R^3$ is chosen from hydrogen, alkyl, alkenyl, aryl, heterocyclyl and hydroxyalkyl;
$R^4$ is chosen from hydrogen, hydroxy, amino, alkoxy, $C_1$-$C_{20}$ alkyl and $C_1$-$C_{20}$ alkyl substituted with hydroxy or carbonyl;
$R^5$ is selected from hydrogen, hydroxyl, alkoxy and alkyl;
$R^6$ is chosen from hydrogen, hydroxy, alkoxy and —NR$^{10}$R$^{11}$; or together, $R^5$ and $R^6$ form a carbonyl or a vinyl substituent;
$R^{10}$ and $R^{11}$ are chosen independently from hydrogen, alkyl and aliphatic; and,
═══ represents a single or double bond.

As such, the present invention provides methods of reducing antipsychotic induced weight gain induced by atypical antipsychotic medications in a patient. The method comprises administration of a therapeutically effective amount of a compound of Formula I to the patient in need thereof, preferably, Compound 1.

In one aspect, the invention relates to the lowering of circulating ghrelin levels and/or the levels of ghrelin in gastrointestinal tracts. As such, the present invention is further directed to methods of suppressing food intake comprising administering to the patient in need of treatment an effective amount of the compounds of Formula I, wherein the increased appetite is induced by administration of an atypical antipsychotic.

In one embodiment, the induced weight gain is associated with administration of olanzapine, clozapine, risperidone, quetiapine, aripiprazole, ziprasidone, and pharmaceutically acceptable salts thereof. In one aspect, the patient undergoing treatment is suffering from schizophrenia, bipolar disorder, acute mania, major depression or psychotic agitation or palliative care or is in need of terminal sedation.

In another embodiment, the compounds of Formula I are administered orally to the patient in need of treatment at a daily dose of about 3 to 30 mg/day, more preferably about 3 to 15 mg/day, even more preferably 5 mg/day. In another aspect, the compounds of Formula I are administered prior to the administration of an atypical antipsychotic or after the administration of an atypical antipsychotic, or along with the administration of an atypical antipsychotic or prior to the onset of the antipsychotic induced weight gain or at the start of the patient's atypical antipsychotic treatment. In one embodiment, the compounds of Formula I are administered daily. In some embodiments, the patient receiving daily administration of a compound of Formula I also receives a daily administration of an atypical antipsychotic.

In still another embodiment, the patient within the past week, month or year of atypical antipsychotic treatment has gained about 5, 10, 15, or 20% body weight.

In another embodiment, the invention relates to a composition comprising a compound of Formula I and an antipsychotic, preferably selected from olanzapine, clozapine, risperidone, quetiapine, aripiprazole and ziprasidone.

DETAILED DESCRIPTION OF INVENTION

Figure 1:
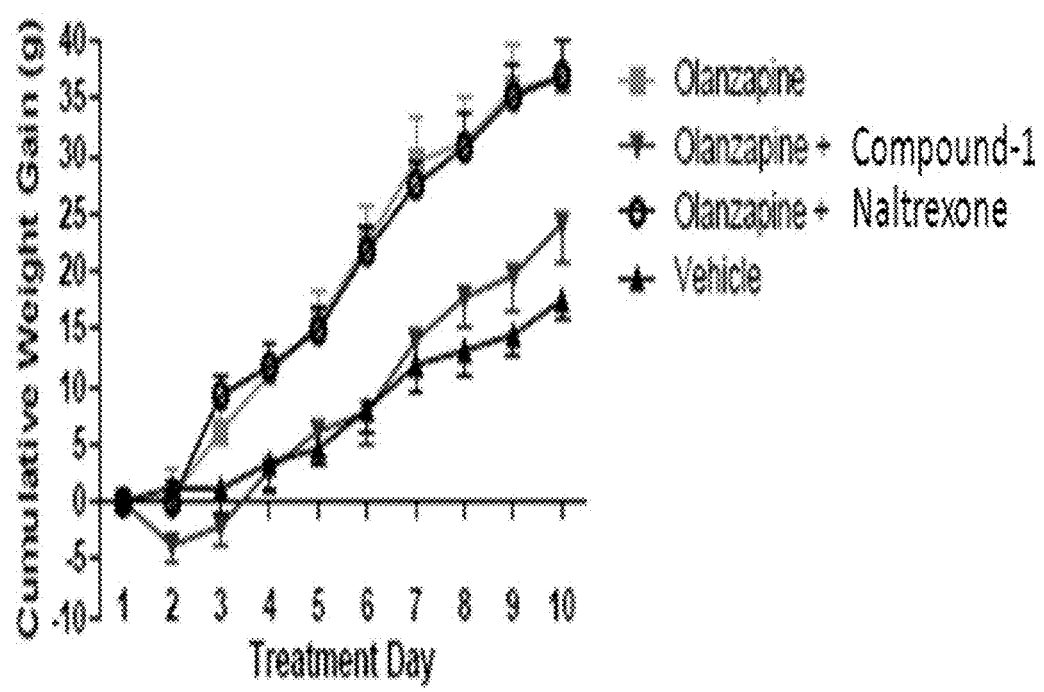
FIG. 1: Evaluation of Compound 1 on olanzapine-related weight gain in female rats. Mean cumulative weight gain of female rats on olanzapine alone, naltrexone+olanzapine and Compound1+olanzapine as a function of days is shown.

The present invention relates to compounds of Formula I:

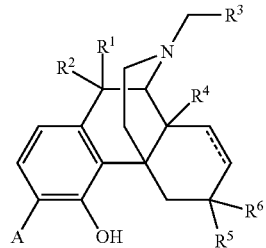

Formula I
wherein, A is chosen from —C(=O)NH$_2$ and —C(=S)NH$_2$;
$R^1$ and $R^2$ are both hydrogen or taken together $R^1$ and $R^2$ are =O;
$R^3$ is chosen from hydrogen, alkyl, alkenyl, aryl, heterocyclyl and hydroxyalkyl;

$R^4$ is chosen from hydrogen, hydroxy, amino, alkoxy, $C_1$-$C_{20}$ alkyl and $C_1$-$C_{20}$ alkyl substituted with hydroxy or carbonyl;
$R^5$ is selected from hydrogen, hydroxyl, alkoxy and alkyl;
$R^6$ is chosen from hydrogen, hydroxy, alkoxy and —NR$^{10}$R$^{11}$; or together, $R^5$ and $R^6$ form a carbonyl or a vinyl substituent;
$R^{10}$ and $R^{11}$ are chosen independently from hydrogen, alkyl and aliphatic; and
===== represents a single or double bond.

In a preferred embodiment, compounds of the invention are related to compounds of Formula II:

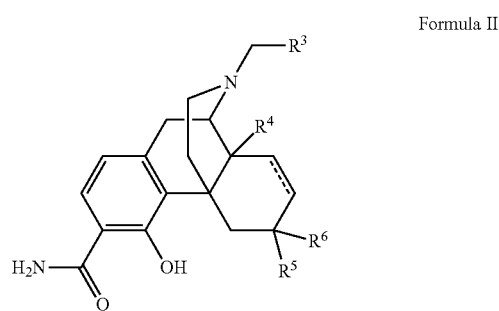

Formula II wherein, $R^3$, $R^4$, $R^5$, and $R^6$ are as defined above.

A more preferred embodiment is a compound of Formula I or II wherein,
$R^4$ is selected from hydrogen and hydroxyl;
$R^5$ is selected from hydrogen, and hydroxyl; and,
$R^6$ is hydrogen;
or together, $R^5$ and $R^6$ form a carbonyl or a vinyl substituent.

A more preferred embodiment is a compound of Formula I or II, wherein $R^3$ is selected from, hydrogen, cyclopropyl, cyclobutyl, vinyl, furan and tetrahydrofuran.

In a preferred embodiment, compounds of the invention are selected from Table A:

TABLE A

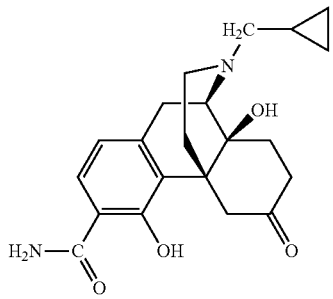 [SMILES: NC(=O)c1ccc2c(c1O)[C@]13CCN(CC4CC4)[C@H](C2)[C@]1(O)CCC(=O)C3]

1

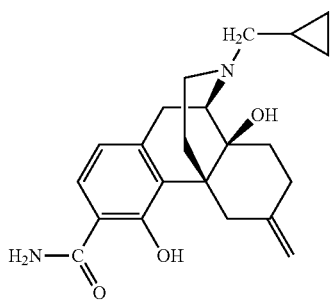 [SMILES: C=C1CC[C@@]2(O)[C@H]3Cc4ccc(C(N)=O)c(O)c4[C@@]2(CCN3CC2CC2)C1]

2

TABLE A-continued
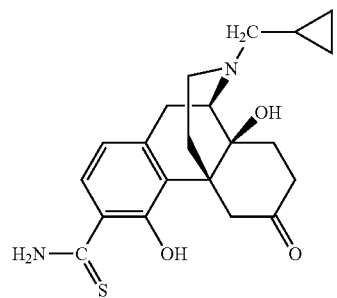 [SMILES: NC(=S)c1ccc2c(c1O)[C@]13CCN(CC4CC4)[C@H](C2)[C@]1(O)CCC(=O)C3]
3
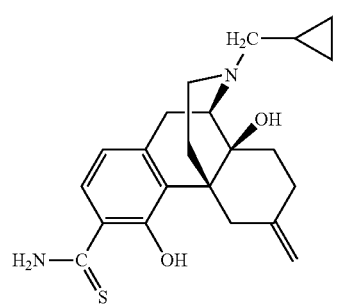 [SMILES: C=C1CC[C@@]2(O)[C@H]3Cc4ccc(C(N)=S)c(O)c4[C@@]2(CCN3CC2CC2)C1]
4
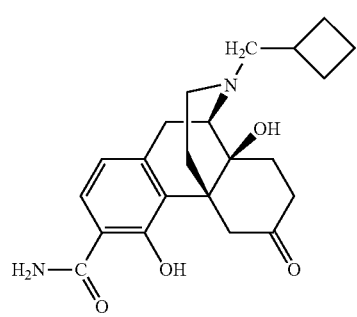 [SMILES: NC(=O)c1ccc2c(c1O)[C@]13CCN(CC4CCC4)[C@H](C2)[C@]1(O)CCC(=O)C3]
5
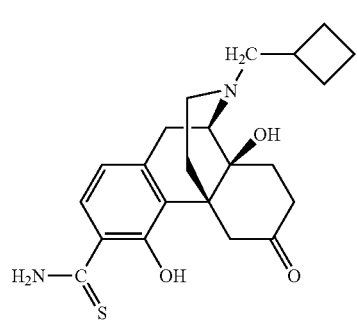 [SMILES: NC(=S)c1ccc2c(c1O)[C@]13CCN(CC4CCC4)[C@H](C2)[C@]1(O)CCC(=O)C3]
6
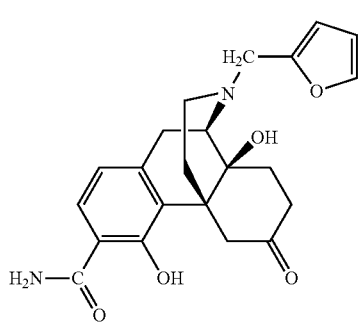 [SMILES: NC(=O)c1ccc2c(c1O)[C@]13CCN(Cc4ccco4)[C@H](C2)[C@]1(O)CCC(=O)C3]
7
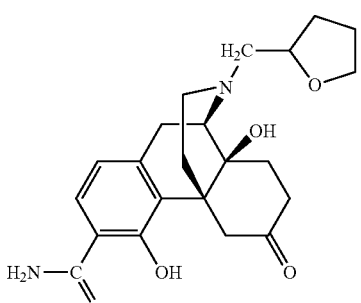
8
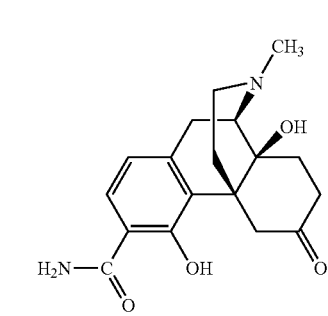 [SMILES: CN1CC[C@]23CC(=O)CC[C@@]2(O)[C@H]1Cc1ccc(C(N)=O)c(O)c13]
9
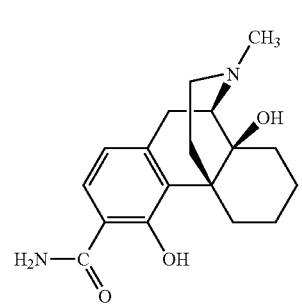 [SMILES: CN1CC[C@]23CCCC[C@@]2(O)[C@H]1Cc1ccc(C(N)=O)c(O)c13]
10
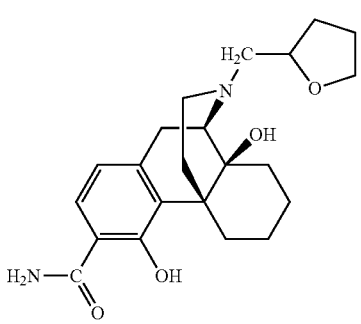 [SMILES: NC(=O)c1ccc2c(c1O)[C@@]13CCCC[C@@]1(O)[C@@H](C2)N(CC1CCCO1)CC3]
11
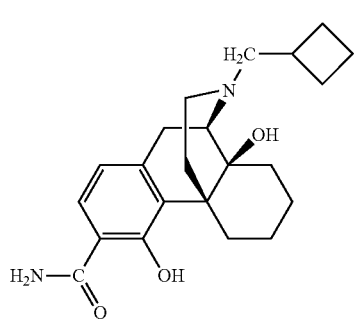 [SMILES: NC(=O)c1ccc2c(c1O)[C@@]13CCCC[C@@]1(O)[C@@H](C2)N(CC1CCC1)CC3]
12

TABLE A-continued

| | |
|---|---|
| 13 | [Structure: N-CH2-cyclopropyl morphinan with H2N-C(=O)- and OH substituents, OH at bridgehead] |
| 14 | [Structure: N-CH3 morphinan with H2N-C(=O)- and OH substituents, OH at bridgehead, with ring double bond and OH] |
| 15 | [Structure: N-CH2-cyclobutyl morphinan with H2N-C(=O)- and OH substituents, OH at bridgehead, and OH] |
| 16 | [Structure: N-allyl morphinan with H2N-C(=O)- and OH substituents, OH at bridgehead, and ketone (=O)] |
| 17 | [Structure: N-(3-methyl-2-butenyl) morphinan with H2N-C(=O)- and OH substituents, and ketone (=O)] |
| 18 | [Structure: N-allyl morphinan with H2N-C(=O)- and OH substituents, OH at bridgehead, ring double bond, and OH] |

Antipsychotic drug therapy is a fundamental tool in the treatment of schizophrenia, bipolar disorder, dementia, acute mania, major depression, psychotic agitation and several non-psychotic mental and neurological conditions. Excessive body weight gain was reported during the 1950's as an adverse effect of typical antipsychotic drug treatment, but the magnitude of body weight gain was found to be higher with the atypical antipsychotic drugs that were introduced after 1990. Atypical antipsychotic drugs such as aripiprazole, clozapine, olanzapine, risperidone, quetiapine, ziprasidone, amusulpride, zotepine and seritindole convey fewer neurological adverse side effects than the typical agents, however, the adverse bodyweight gain associated with atypical treatment has a negative impact on other components of the metabolic profile, such as serum glucose levels, triglyceride and high-density cholesterol levels. The mechanisms by which atypical antipsychotic drugs cause weight gain are not clear. Atypical antipsychotic drugs may increase appetite stimulation by either modifying the function of the appetite system i.e., indices of satiety or by targeting neurochemical physiology and metabolic function i.e., modulation of known hormone targets involved in appetite regulation, such as leptin and ghrelin.

Applicants have surprisingly discovered that compounds of Formula I, a group of opioid modulators are effective in reducing pharmacologically induced weight gain associated with atypical antipsychotic use. As used herein, the term "opioid modulator" refers to compounds that can act as an agonist, antagonist or partial agonist at opioid receptors throughout the body. In one aspect, some of the compounds of Formula I, in particular Compound 1, acts as a mu-opioid receptor antagonist and partial agonist/antagonist at kappa and delta receptors.

As used herein, the term "reducing" refers to any indicia of success in the prevention or reduction of weight gain in a patient induced by an atypical antipsychotic medication. The prevention or reduction of atypical-induced weight gain can be measured based on objective parameters, such as the results of a physical examination. For example, patients undergoing atypical antipsychotic treatment were able to maintain a healthful weight range when given Compound 1. As used herein, a "healthful weight range" refers to a body mass index (BMI) between 19 and 25, as defined by the first Federal guidelines on the identification, evaluation, and treatment of overweight and obesity developed by the National Heart, Lung, and Blood Institute, in cooperation with the National Institute of Diabetes and Digestive and Kidney Diseases (Clinical Guidelines on the Identification, Evaluation, and Treatment of Overweight and Obesity in Adults: Evidence Report, 1998).

Weight gain as a result of prolonged atypical treatment can be determined based on comparison of changes in a patient's body weight during the course of treatment. The weight gained may also be reflected in an increased body fat percentage. To be considered to have gained weight as a result of atypical treatment, weight gain may be measured by a percentage increase in weight during atypical treatment, e.g., an increase of body weight by at least 2%, 5%, 10%, 15%, 20%, 25%, 30%, 35% or 40%, over, for example, a ten-week period of atypical treatment. An increase in body fat percentage may also be used to measure weight gain, e.g., an increase of body fat percentage by at least 2%, 5%, 10%, or 15% over, for example, a ten-week period of atypical treatment. Weight gain as a result of atypical treatment can occur as soon as the patient begins the atypical treatment regime i.e., within days or weeks or the period can be more prolonged i.e., months or within a year.

As used herein, the term "atypical" refers to the newer class of antipsychotic agents that have reduced extrapyramidal side effects in comparison with traditional antipsychotic medications such as chloropromazine, loxapine, haloperidol, fluphenazine, etc. Examples of such atypical antipsychotics include, but are not limited to, amisulpride, aripiprazole, asenapine, blonanserin, bifeprunox, clotiapine, clozapine, iloperidone, lurasidone, mosapramine, melperone, olanzapine, paliperidone, perospirone, pimavanserin, quepin, quetiapine, remoxipride, risperidone, sertindole, sulpiride, vabicaserin, ziprasidone, and zotepine.

Compounds of Formula I are particularly useful for the treatment of weight gain associated with atypical antipsychotics, including, but not limited to, amisulpride, aripiprazole, asenapine, blonanserin, bifeprunox, clotiapine, clozapine, iloperidone, lurasidone, mosapramine, melperone, olanzapine, paliperidone, perospirone, pimavanserin, quepin, quetiapine, remoxipride, risperidone, sertindole, sulpiride, vabicaserin, ziprasidone, and zotepine. It is understood that the present invention includes all pharmaceutically acceptable salts, hydrates, solvates, and polymorphs of the above drugs in combination with compounds of Formula I and its salts, hydrates, solvates and polymorphs.

Preferred atypical antipsychotics of the present invention include: Olanzapine, 2-methyl-4-(4-methyl-1-piperazinyl)-10H-thieno[2,3-b][1,5]benzodiazepine, and its preferred crystal form II is a known compound and is described in U.S. Pat. Nos. 5,229,382 and 5,736,541 as being useful in the treatment of schizophrenia, schizophreniform disorder, acute mania, mild anxiety states, and psychosis.

Clozapine, 8-chloro-11-(4-methylpiperazin-1-yl)-5H-dibenzo[b,e][1,4]diazepine, is described in U.S. Pat. No. 3,539,573. Clinical efficacy in the treatment of schizophrenia is described in (Hanes, et al, *Psychopharmacol. Bull.*, 24, 62 (1988)).

Risperidone, 4-[2-[4-(6-fluorobenzo[d]isoxazol-3-yl)-1-piperidyl]ethyl]-3-methyl-2,6-diazabicyclo[4.4.0]deca-1,3-dien-5-one, and its use in the treatment of psychotic diseases are described in U.S. Pat. No. 4,804,663.

Quetiapine, 2-(2-(4-dibenzo[b,f][1,4]thiazepine-11-yl-1-piperazinyl)ethoxy)ethanol, and its activity in assays, which demonstrate utility in the treatment of schizophrenia are described in U.S. Pat. No. 4,879,288. Quetiapine is typically administered as its (E)-2-butenedioate (2:1) salt.

Aripiprazole, 7-[4-[4-(2,3-dichlorophenyl) piperazin-1-yl]butoxy]-3,4-dihydro-1H-quinolin-2-one and its utility in the treatment of schizophrenia are described in U.S. Pat. No. 5,006,528.

Ziprasidone, 5-[2-[4-(1,2-benzisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031.

The patient, as used herein is preferably a mammal, with human patients especially preferred, is suffering from a mental illness treatable with an atypical antipsychotic medication. Typical disease states treatable with antipsychotic medication include, but are not limited to, schizophreniform disorder, schizoaffective disorder, severe schizoaffective disorder with psychotic features, bipolar I disorders with a single manic episode, severe bipolar I disorders with psychotic features, bipolar I disorders manifesting a mixed most recent episode, severe bipolar I disorders with psychotic features, brief psychotic disorders, psychotic disorders NOS, paranoid personality disorders, schizoid personality disorders, schizophrenia, schizotypal personality disorders with sedative, hypnotic, or anxiolytic manifestations, major depressive disorders with psychotic features, dementia, acute mania, psychotic agitation, unipolar disorder and psychotic disorders due to specific general medical conditions.

The methods of this invention reduce atypical antipsychotic induced weight gain. The amount of compounds of Formula I, adequate to accomplish this is defined as a "therapeutically effective dose". The dosage schedule and amounts effective for this use, i.e., the "dosing regimen," will depend upon a variety of factors, including the type of the atypical antipsychotic medication the patient is using, the amount of atypical-induced weight gain that has already occurred, the patient's physical status, age and the like. In calculating the dosage regimen for a patient, the mode of administration also is taken into consideration.

Suitable daily oral dosages for the compounds of Formula I described herein are on the order of about 1.0 mg to about 50 mg. Desirably, each oral dosage contains from 1.0 to 50 mgs, particularly 1.0, 2.5, 5, 10, 15, 20, 25, 30, 40 and 50 milligrams of the compounds of Formula I are administered for the treatment atypical-induced weight gain. In a preferred embodiment, the compounds of Formula I are administered in a dose range of about 3.0 mgs to about 30 mgs per day, more preferably about 3.0 mgs to about 15 mgs per day, even more preferably about 5 mgs per day. U.S. application Ser. No. 12/727,784, filed on Mar. 19, 2010, describing the therapeutic dosing range of carboxamide substituted morphinans is hereby incorporated by reference. Dosage regimen may be adjusted to provide the optimal therapeutic response. The specific dose level for any particular patient will vary depending upon a variety of factors, including but not limited to, the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The compounds of Formula I can be administered in such oral forms as tablets, capsules (each of which includes sustained release or timed release formulations), pills, powders, granules, elixirs, tinctures, suspensions, syrups, and emulsions. The present invention includes the use of both oral rapid-release and time-controlled release pharmaceutical formulations (see, e.g., U.S. Pat. Nos. 6,495,166; 5,650, 173; 5,654,008 which describes controlled release formulations and is incorporated herein by reference).

In another embodiment, the invention relates a composition comprising a compound of Formula I and an antipsychotic, preferably selected from olanzapine, clozapine, risperidone, quetiapine, aripiprazole and ziprasidone. In a more preferred embodiment a compound of Formula I is selected from Table A. In a more preferred embodiment, the invention relates to a composition comprising a compound of Table A and an antipsychotic selected from olanzapine, clozapine, risperidone, quetiapine, aripiprazole and ziprasidone.

The compounds of Formula I can be administered in a mixture with pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the compounds of Formula I can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents, coloring and flavoring agents can also be incorporated into the mixture. Stabilizing agents such as antioxidants (BHA, BHT, propyl gallate, sodium ascorbate, citric acid) can also be added to stabilize the dosage forms. Other suitable components include gelatin, sweeteners, natural and synthetic gums such as acacia, tragacanth or alginates, carboxymethylcellulose, polyethylene glycol, waxes and the like. For a discussion of dosing forms, carriers, additives, pharmacodynamics, etc., see Kirk-Othmer *Encyclopedia of Chemical Technology*, Fourth Edition, 1996, 18:480-590, incorporated herein by reference.

DEFINITIONS

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The term "hydroxyalkyl" as used herein refers to an alkyl substituent, as defined herein, wherein one or more hydrogens are replaced with an —OH group.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety. The invention is further illustrated by the following non-limited examples.

EXAMPLE 1

Evaluation of Compound 1 on Olanzapine-Related Weight Gain in Female Rats

To determine if Compound 1 could reduce antipsychotic associated weight gain, four groups of female rats (n=8/group) were used for this study: 1) olanzapine only; 2) olanzapine and naltrexone; 3) olanzapine and Compound1; and 4) vehicle control. The rats were assigned to treatment groups using a random block design based on initial body weight. The olanzapine group was given PO twice daily (6 hours between doses) at a dose of 1 mg/kg (in 1% methylcellulose, for 10 consecutive days). Naltrexone and Compound 1 were both administered at doses of 2 mg/kg (SC) concurrent with the afternoon administration of olanzapine. There was an effect of Treatment ($F_{(3,28)}$=9.7, p<0.001), Day ($F_{(3,9)}$=359.8, p<0.001) and a Treatment×Day interaction ($F_{(27,252)}$=10.2, p<0.001) on body weight. While all rats gained weight during the study, olanzapine alone administration caused greater increases in weight gain and the increased gain was apparent by day 5. Co-administration of naltrexone with olanzapine did not affect olanzapine-induced weight gain. In contrast, weight gain in rats receiving Compound 1 was similar to those in vehicle-controls rats, demonstrating the ability of Compound1 to block olanzapine induced weight gain (FIG. 1).

EXAMPLE 2

Evaluation of Compound1 and Naltrexone on Circulating Ghrelin Levels

Figure 2:
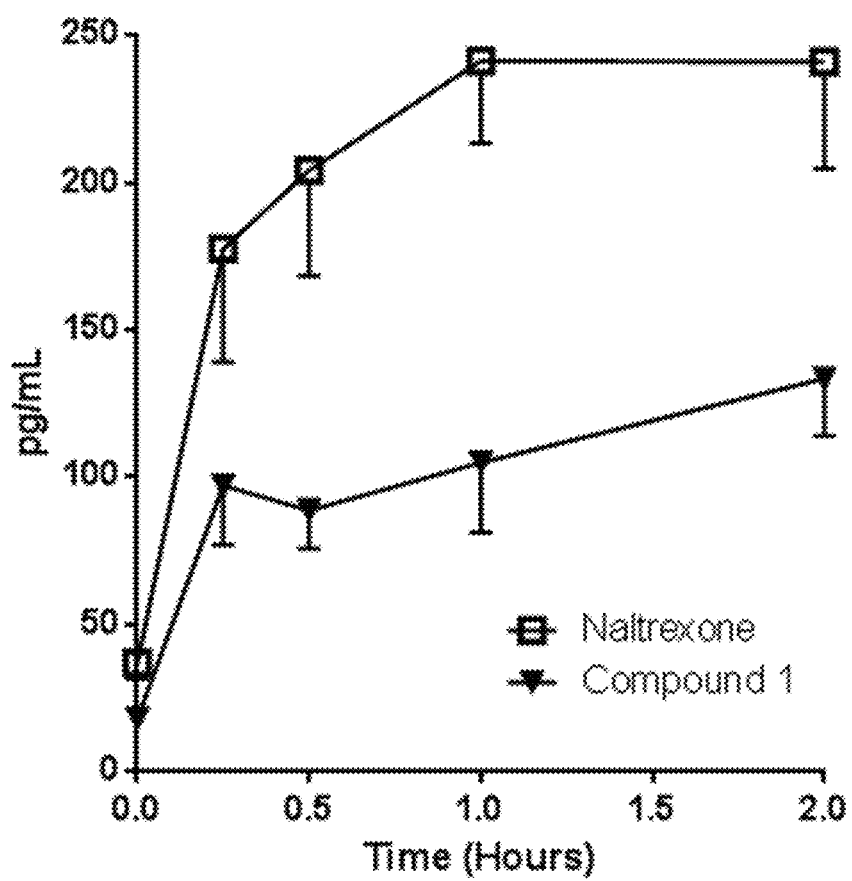
FIG. 2: Evaluation of Compound 1 and naltrexone on circulating ghrelin levels (pg/mL) as a function of time (hours) is shown.

Recent research has reported that the gut hormone ghrelin plays a role in appetite regulation by targeting the brain to promote food intake and adiposity (Chaudhri O, et al., *Philos Trans R Soc Lond B Biol Sci.* 2006 Jul. 29; 361 (1471):1187-209; Abizaid A, et al., *J. of Clin. Invest.* 116: 3229-3239.) It is also known in literature that olanzapine increases circulating ghrelin levels. To determine whether Compound1 and naltrexone have any effect on circulating levels of ghrelin, conscious, unrestrained rats (low stress model) were administered Compound 1 and nalrextone (10 mg/kg, PO). Blood samples were collected and analyzed by bioanalytical for circulating levels of ghrelin at 0, 15, 30, 60, and 120 minutes most administration. Results indicated that naltrexone had significantly greater circulating ghrelin levels than Compound 1 two hours post administration (FIG. 2).

EXAMPLE 3

Evaluation of Olanzapine-Related Changes in Non-Human Primates

The purpose of the study was to evaluate if changes in body weight can be assessed in female cynomolgus monkeys after twice daily oral (gavage) treatment with olanzapine and if changes were observed, can once a day intramuscular co-administration of Compound 1 mitigate or attenuate any of these changes. Clinical observations and weight gain were assessed over a 28-day treatment period.

Three groups of late-adolescent female cynomolgus monkeys (n=5/group; 4.04 assessed in female cynomolgus monkeys after 120 minutes most admolanzapine only; and 3) olanzapine with Compound 1. Beginning two weeks prior to the study, monkeys were given ad libitum access to a highly palatable, high caloric diet. On the day prior to the start of treatment, monkeys were weighed and assigned to groups using a randomized block design based on body weight (BW); average BW across the 3 groups was 3.1±0.08 kg on the day of randomization. Also, baseline whole body CT scans were taken on the day prior to initiation of treatments. Monkeys receiving olanzapine were dosed twice daily (6 hours between doses) for 28 days. The initial daily dose of olanzapine was 1 mg/kg (PO, in 1% methylcellulose) and increased every 3 days to a daily dose of 6 mg/kg by Day 10. For group 3, Compound 1 (0.4 mg/kg, IM) was administered in the morning immediately after administration of olanzapine. Weights were taken every 3 days and on Day 28 blood samples were collected for serum chemistry analysis. A second CT scan was conducted on day 29.

Figure 5:
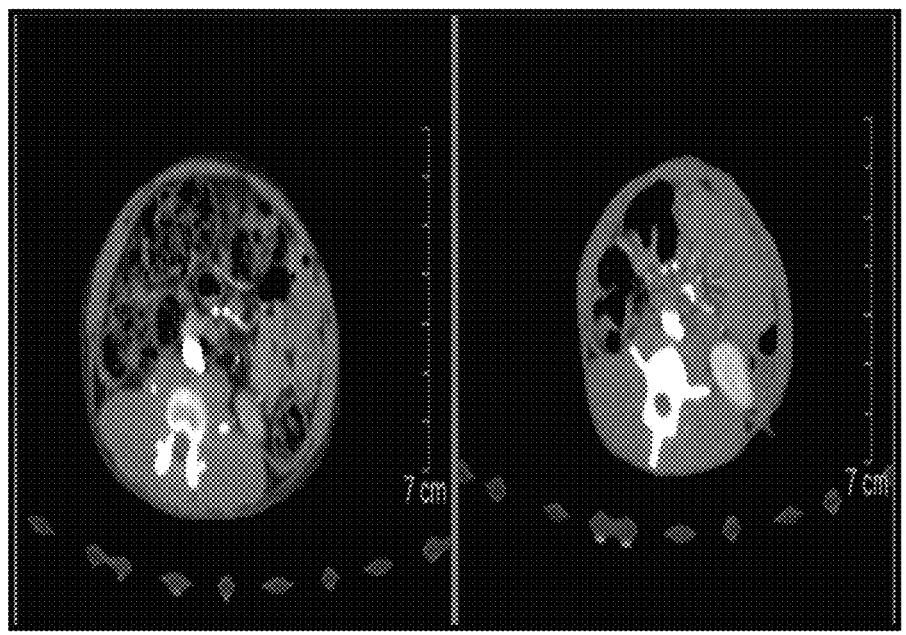
FIG. 5: (a) CT scan evaluation of olanzapine induced weight gain on abdominal fat distribution in female cynomolgus monkeys treated with olanzapine; (b) CT scan evaluation of olanzapine induced weight gain on abdominal fat distribution in female cynomolgus monkeys treated with olanzapine and Compound 1.
Figure 5:
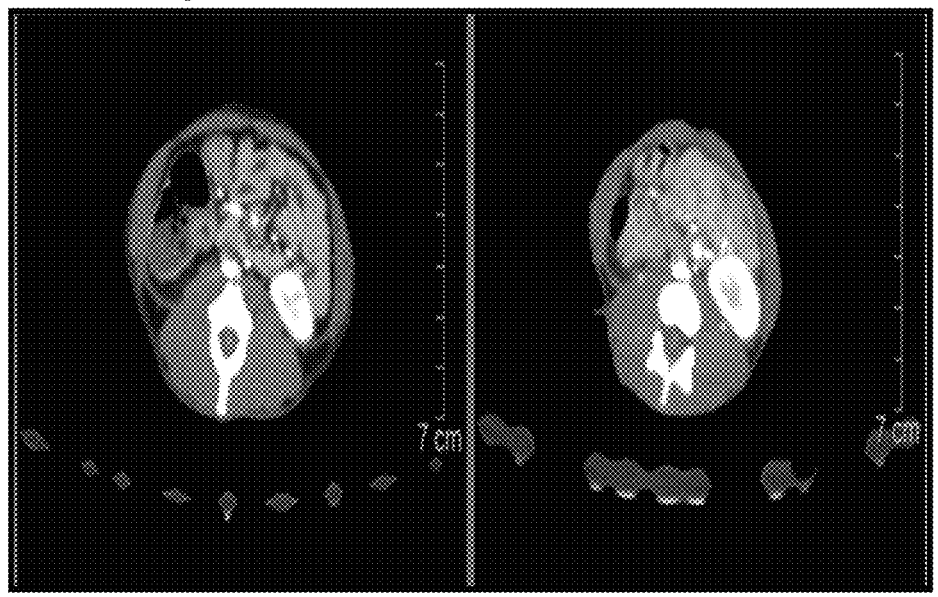
Figure 6:
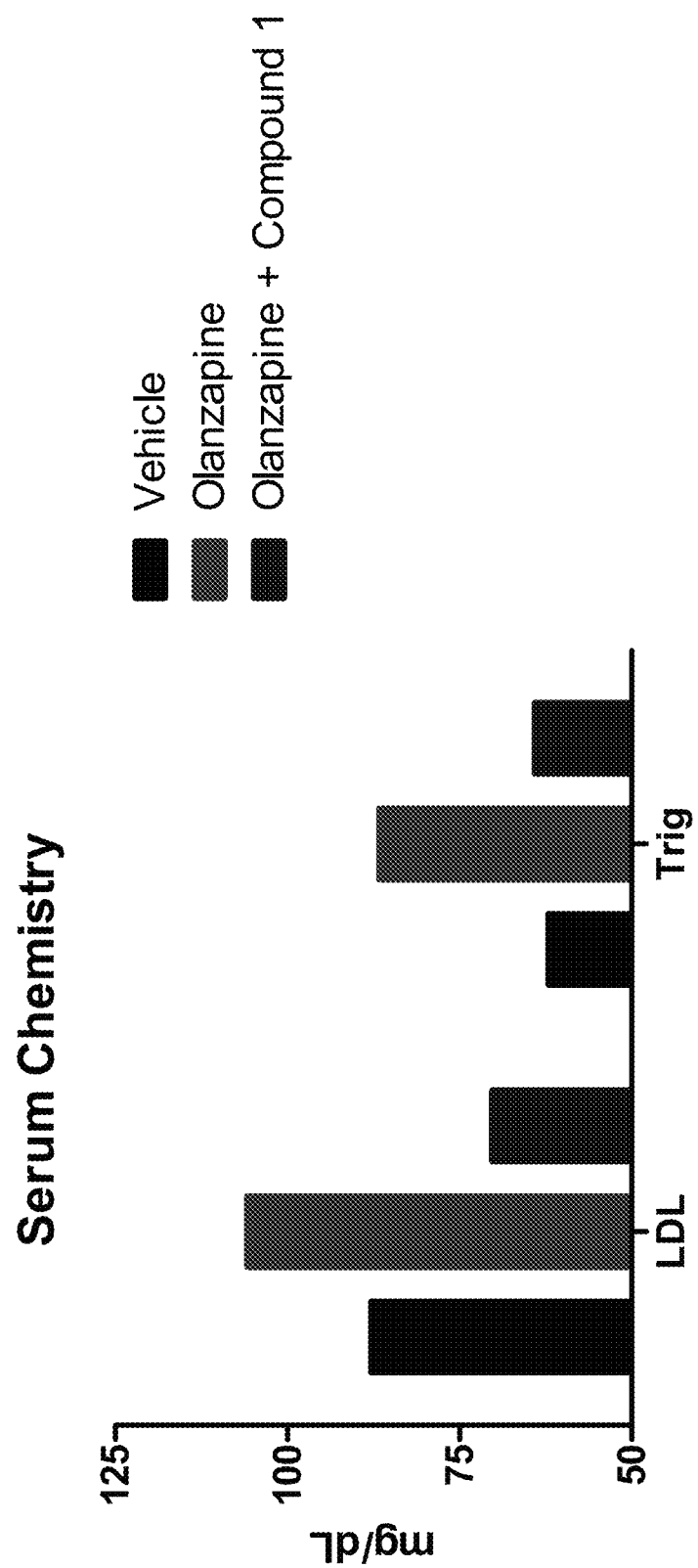
FIG. 6: Evaluation of blood serum chemistry analysis on female cynomolgus monkeys treated with and without Compound 1.

Results indicated that BWs were relatively constant for two months prior to the initiation of ad libitum feeding. Vehicle treated monkeys gained an average of 0.28 kg (9% of Day 0 BW) over the 28-day study. This gain was attributed to the ad libitum feeding of the highly palatable diet. Over the same 28-day period, olanzapine-treated monkeys gained an average of 0.46 kg (15% of Day 0 BW). This marked increase in average weight gain was driven by 3 of the 5 monkeys who gained between 19.8 and 37.8% of their initial body weight. An accretion of adipose tissue was observed in all monkeys compared to baseline control values. However, monkeys in the olanzapine group gained relatively more adipose tissue compared to the vehicle group. Also, there was a difference in the location of the adipose tissue deposition with the olanzapine group showing more abdominal fat accretion (FIG. 5). Concentrations of triglycerides (TGs) and LDL were higher in olanzapine treated animals (86.6 and 105.8 mg/dL, respectively) compared to the vehicle group (62 and 87.8 mg/dL, respectively) (FIG. 6). In monkeys treated with olanzapine and Compound 1, the average BW gain over the 28 days was only 0.08 kg (2.6% of Day 0 BW). While these animals also gained adipose tissue, the extent and distribution of fat was similar to that observed in the vehicle group and lower than the olanzapine-only group. Finally, co-administration of Compound 1 prevented olanzapine-induced elevations in TGs and LDL concentrations.

Figure 3:
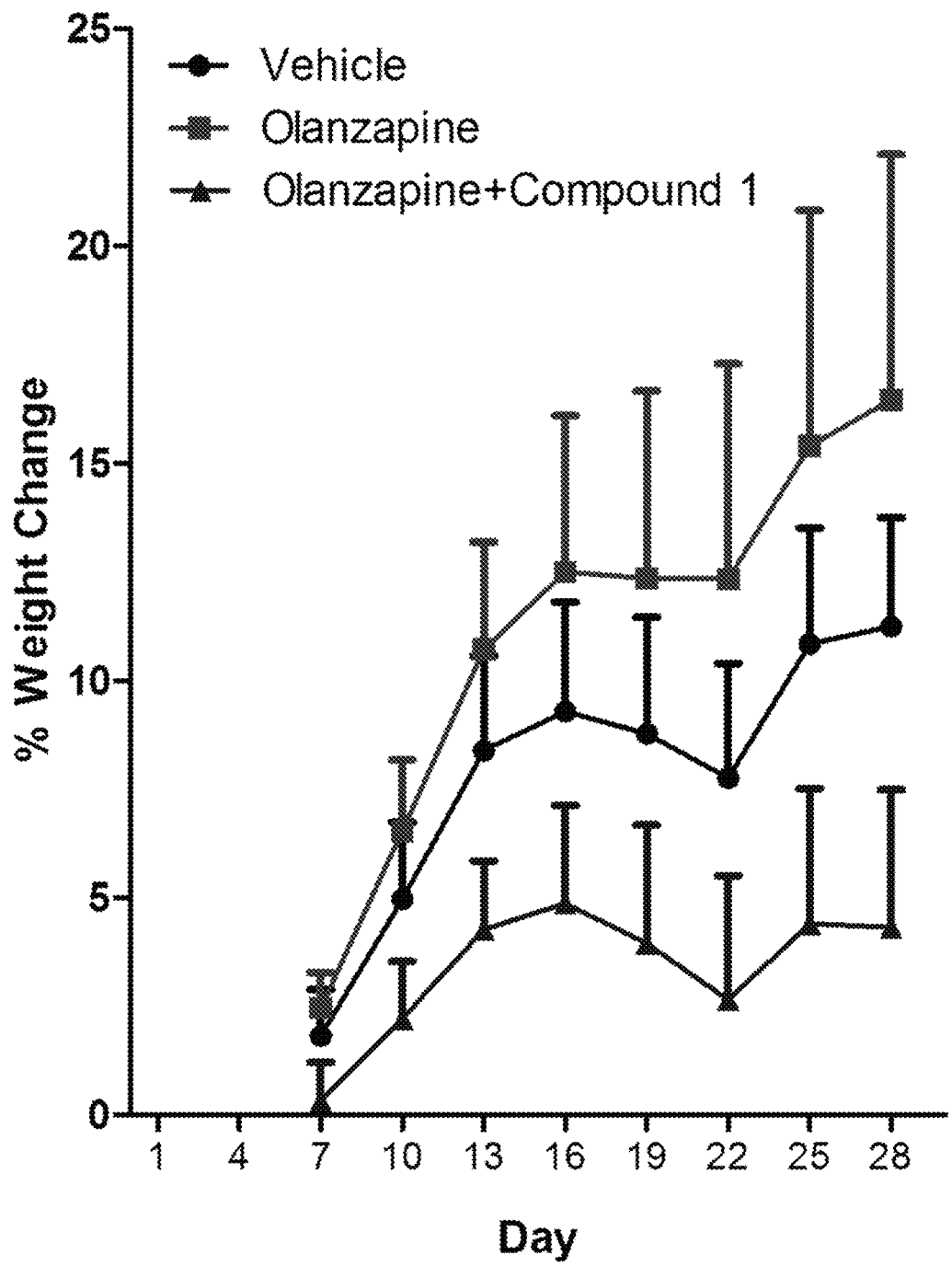
FIG. 3: Evaluation of olanzapine induced weight gain and body composition in female cynomolgus monkeys treated with and without Compound 1.
Figure 4:
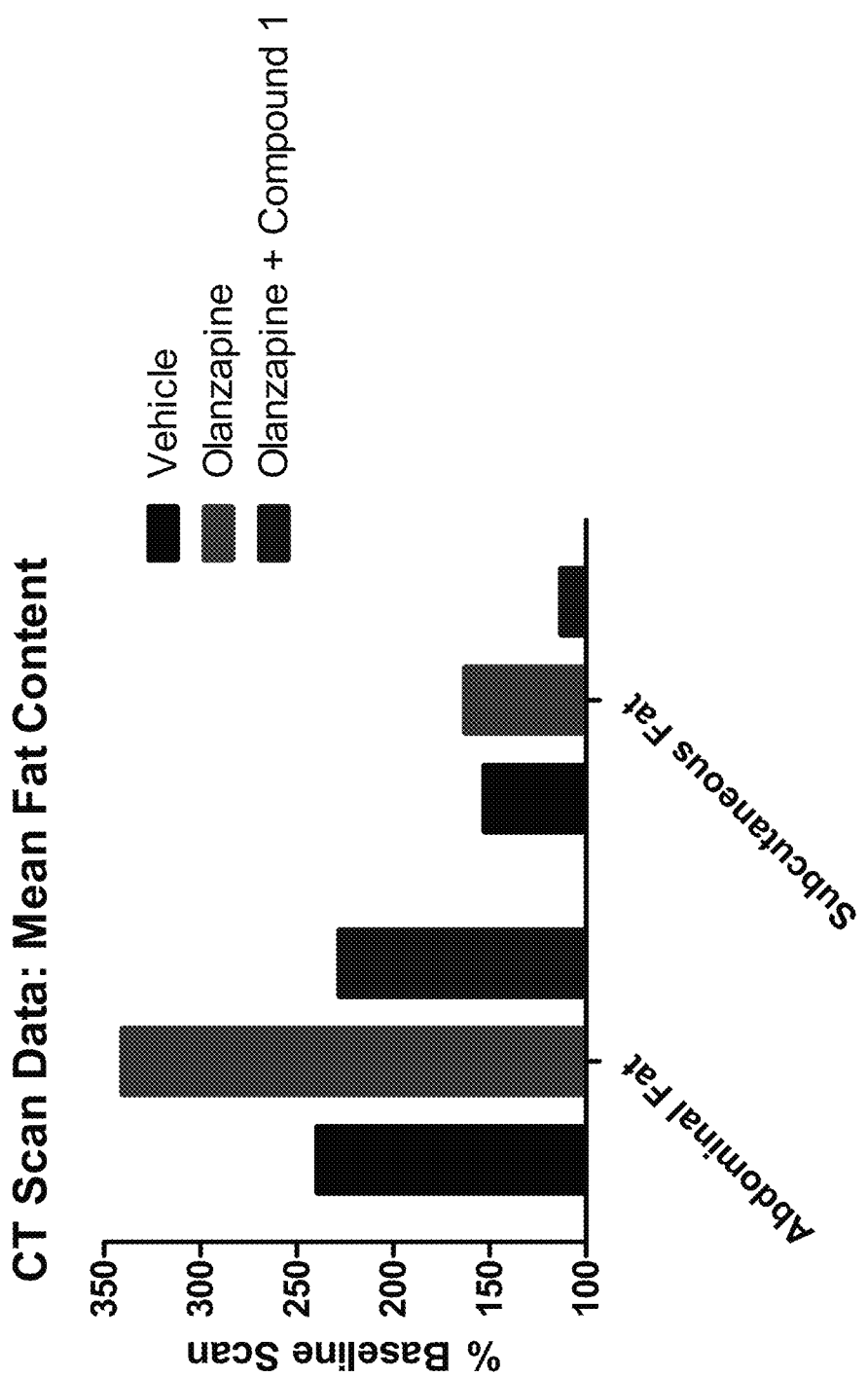
FIG. 4: Change in fat distribution for female cynomolgus monkeys administered with olanzapine with and without Compound 1.

Based on this data, treatment of nonhuman primates with olanzapine for 28 days resulted in qualitative changes in weight, adipose tissue accretion, TGs and LDLs similar to those reported in patients. Furthermore, OLZ-induced changes were mitigated by co-administration of Compound 1 (FIGS. 3 and 4).

Unless otherwise defined, all technical and scientific terms used herein are accorded the meaning commonly known to one with ordinary skill in the art. All publications, patents, published patent applications and other references mentioned herein are hereby incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of reducing diseases or disorders associated with the adverse metabolic profile of olanzapine by administering to a patient in need 10 thereof an effective amount of a compound of the formula:

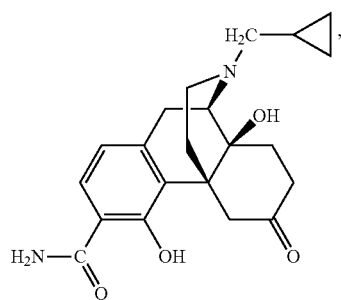 [SMILES: NC(=O)c1ccc2c(c1O)[C@]13CCN(CC4CC4)[C@H](C2)[C@]1(O)CCC(=O)C3]

or a pharmaceutically acceptable salt thereof.

2. The method according to claim 1, wherein said adverse metabolic effects comprise an increase in abdominal fat distribution, serum glucose levels, triglyceride levels or high density cholesterol.

3. The method of claim 1, wherein said disease or disorder is diabetes.

4. The method of claim 1, wherein said diseases or disorders are cardiovascular disorders.

5. The method of claim 1, wherein the disease or disorder is obesity.

6. The method of claim 1, wherein the disease or disorder is hypertension.

7. A method of lowering circulating ghrelin levels in a patient in need thereof, comprising administering to said patient an effective amount of the compound of formula:

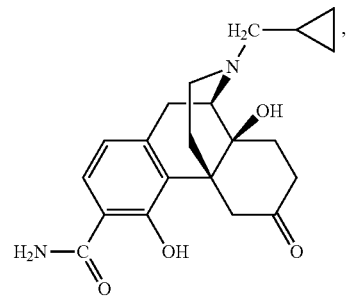

or a pharmaceutically acceptable salt thereof.

8. A method of lowering circulating ghrelin levels in a patient in need thereof, comprising administering to said patient an effective amount of the compound of formula:

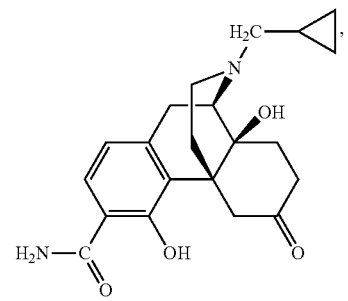 [SMILES: NC(=O)c1ccc2c(c1O)[C@]13CCN(CC4CC4)[C@H](C2)[C@]1(O)CCC(=O)C3]

or a pharmaceutically acceptable salt thereof, wherein said ghrelin level is increased by the administration of an atypical antipsychotic.

9. The method according to claim 8, wherein said atypical antipsychotic is olanzapine.

10. A method of lowering ghrelin levels in gastrointestinal tracts of a patient in need thereof, comprising administering to said patient an effective amount of the compound of formula:

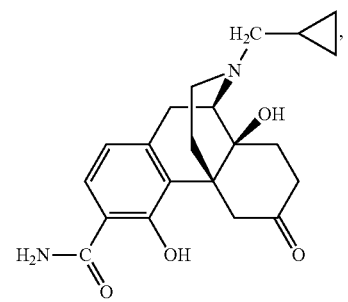 [SMILES: NC(=O)c1ccc2c(c1O)[C@]13CCN(CC4CC4)[C@H](C2)[C@]1(O)CCC(=O)C3]

or a pharmaceutically acceptable salt thereof.

11. A method of lowering ghrelin levels in gastrointestinal tracts of a patient in need thereof, comprising administering to said patient an effective amount of the compound of formula:

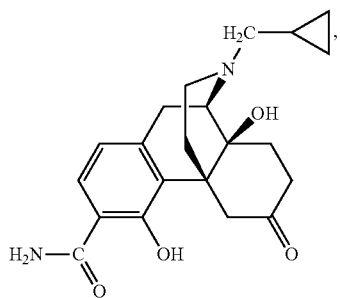 [SMILES: NC(=O)c1ccc2c(c1O)[C@]13CCN(CC4CC4)[C@H](C2)[C@]1(O)CCC(=O)C3]
or a pharmaceutically acceptable salt thereof, wherein said ghrelin level is increased by the administration of an atypical antipsychotic.
12. The method according to claim 11, wherein said atypical antipsychotic is olanzapine.
* * * * *

UNITED STATES PATENT AND TRADEMARK OFFICE
CERTIFICATE OF CORRECTION

| | | |
|---|---|---|
| PATENT NO. | : 9,517,235 B2 | Page 1 of 1 |
| APPLICATION NO. | : 14/813260 | |
| DATED | : December 13, 2016 | |
| INVENTOR(S) | : Daniel Deaver and Mark Todtenkopf | |

It is certified that error appears in the above-identified patent and that said Letters Patent is hereby corrected as shown below:

Column 15, Claim 1, Line 40, please delete "10" appearing between the words need and thereof.

Signed and Sealed this
Twenty-first Day of March, 2017

Michelle K. Lee
*Director of the United States Patent and Trademark Office*